(12) United States Patent
Tal

(10) Patent No.: US 6,716,228 B2
(45) Date of Patent: Apr. 6, 2004

(54) SURGICAL ACCESS DEVICE

(75) Inventor: Michael G. Tal, Woodbridge, CT (US)

(73) Assignee: Yale University, New Haven, CT (US)

( * ) Notice: Subject to any disclaimer, the term of this patent is extended or adjusted under 35 U.S.C. 154(b) by 77 days.

(21) Appl. No.: 09/946,348

(22) Filed: Sep. 6, 2001

(65) Prior Publication Data

US 2002/0040231 A1 Apr. 4, 2002

Related U.S. Application Data

(60) Provisional application No. 60/237,062, filed on Sep. 30, 2000.

(51) Int. Cl.[7] ............................................... A61B 17/32
(52) U.S. Cl. ....................................... 606/167; 606/185
(58) Field of Search ................................ 606/167, 182, 606/181, 185, 170, 171, 172, 184, 190, 189; 30/2, 151, 160, 161, 162; 604/168, 164.01, 161, 165.01, 165.02, 247

(56) References Cited

U.S. PATENT DOCUMENTS

| | | | | | |
|---|---|---|---|---|---|
| 3,677,244 A | * | 7/1972 | Hassinger | ................ | 604/161 |
| 4,633,860 A | * | 1/1987 | Korth et al. | ................ | 606/170 |
| 5,370,654 A | * | 12/1994 | Abidin et al. | ................ | 606/182 |
| 5,507,760 A | | 4/1996 | Wynne et al. | ................ | 606/159 |
| 5,545,175 A | * | 8/1996 | Abidin et al. | ................ | 606/182 |
| 5,713,870 A | | 2/1998 | Yoon | ................ | 604/174 |
| 5,843,108 A | * | 12/1998 | Samuels | ................ | 606/167 |
| 5,879,338 A | | 3/1999 | Mahurkar | ................ | 604/195 |
| 6,007,554 A | | 12/1999 | Van Ess | ................ | 606/167 |
| 6,048,354 A | * | 4/2000 | Lawrence | ................ | 606/185 |

* cited by examiner

*Primary Examiner*—Vy Q. Bui
(74) *Attorney, Agent, or Firm*—Welsh & Flaxman

(57) ABSTRACT

A surgical access device includes a hub supporting a needle shaped and dimensioned for penetrating tissue in a desired manner and a surgical blade coupled to the needle for movement along the length of the needle such that the surgical blade may be selectively moved along the needle to incise tissue adjacent the needle.

16 Claims, 4 Drawing Sheets

SURGICAL ACCESS DEVICE

CROSS-REFERENCE TO RELATED APPLICATION

This U.S. patent application is based upon U.S. Provisional Patent Application Ser. No. 60/237,062, filed Sep. 30, 2000, and entitled "SLIDING BLADE VASCULAR ACCESS NEEDLE".

BACKGROUND OF THE INVENTION

1. Field of the Invention

The invention relates to a surgical device. More particularly, the invention relates to a vascular access device including a needle and sliding surgical blade which facilitates vascular access and associated skin incision without the need for retrieval of multiple surgical tools. The present invention further relates to methods for utilizing the present vascular access device.

2. Description of the Prior Art

Vascular access via guidewires and catheters has become a common method for performing a variety of minimally invasive procedures. The use of catheters as a means of accessing the human body helps to minimize trauma that might otherwise take place, and those skilled in the art are continually attempting to develop new procedures and instruments which improve upon and expand treatments.

Most vascular access procedures begin with the insertion of a guidewire to a treatment site. Once the guidewire is properly inserted, the physician may utilize the guidewire to insert and maneuver a catheter to a predetermined treatment site. Insertion of a guidewire and catheter is generally accomplished using a multiple step process involving a separate and distinct needle and surgical blade.

Specifically, the physician first makes an incision at a predetermined treatment site and returns the scalpel to a tray table adjacent the operating table (this may also be done after needle insertion). The access opening created by the initial incision is required to permit entry of the catheter after creation of the skin incision, because the catheter is substantially larger than a common guidewire and needle. The physician then retrieves a traditional needle from the tray adjacent the operating table and inserts the needle into the patient's vascular system at a selected location. Once the needle is properly positioned, the physician maneuvers a guidewire through the needle, into the vascular system and to a predetermined location within the vascular system. When the guidewire is properly positioned, the physician may remove the needle, insert the catheter and move forward with the specific procedure.

The many steps and instruments required during the initial stages of guidewire and catheter insertion make the possibility for mishaps more likely. For example, the physician, or nurse, must take the exposed scalpel from a tray to the patient and back to the tray, thus increasing the risk of injury to the operators and exposure to blood born pathogens such as HIV and Hepatitis B and C viruses. In addition, when one performs skin incisions after the insertion of a needle, there is a possibility that the skin incision is not directly adjacent to the needle. Inaccuracies such as this result in tissue being left between the incision and the needle, prevent insertion of the catheter and require revision of the incision. Current techniques further require that the incision be performed prior to the insertion of the needle into the skin of a patient. This may necessitate additional skin incisions in the event vascular access is not successful and another access site is required.

In view of the many shortcomings associated with the current and prior techniques utilized during the initial insertion of a catheter and/or guidewire, a need currently exists for an efficient and accurate surgical tool for performing these procedures. The present invention provides such a tool.

SUMMARY OF THE INVENTION

It is, therefore, an object of the present invention to provide a surgical access device. The device includes a hub supporting a needle shaped and dimensioned for penetrating tissue in a desired manner and a surgical blade coupled to the needle for movement along the length of the needle such that the surgical blade may be selectively moved along the needle to incise tissue adjacent the needle.

It is also an object of the present invention to provide a surgical access device including a housing positioned adjacent the hub, wherein the housing is shaped and dimensioned for storing the surgical blade when not in use.

It is another object of the present invention to provide a surgical access device wherein the housing includes a slot into which the blade is retracted in its nonuse position.

It is a further object of the present invention to provide a surgical access device wherein the housing is substantially cylindrical and surrounds a proximal end of the needle.

It is yet another object of the present invention to provide a surgical access device wherein the surgical blade slides relative to the needle.

It is still a further object of the present invention to provide a surgical access device wherein the surgical blade forms part of a surgical blade assembly.

It is also an object of the present invention to provide a surgical access device wherein the surgical blade assembly includes a through hole through which the needle passes for coupling the needle to the surgical blade.

It is a further object of the present invention to provide a surgical access device wherein the surgical blade assembly includes a handle.

It is also an object of the present invention to provide a method for surgical access. The method is achieved by percutaneously accessing a subject with a needle of a surgical access device to create an access opening, retrieving a surgical blade coupled to the needle from a storage position, and moving the surgical blade relative the needle such that the surgical blade incises tissue adjacent the access opening created by the needle.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
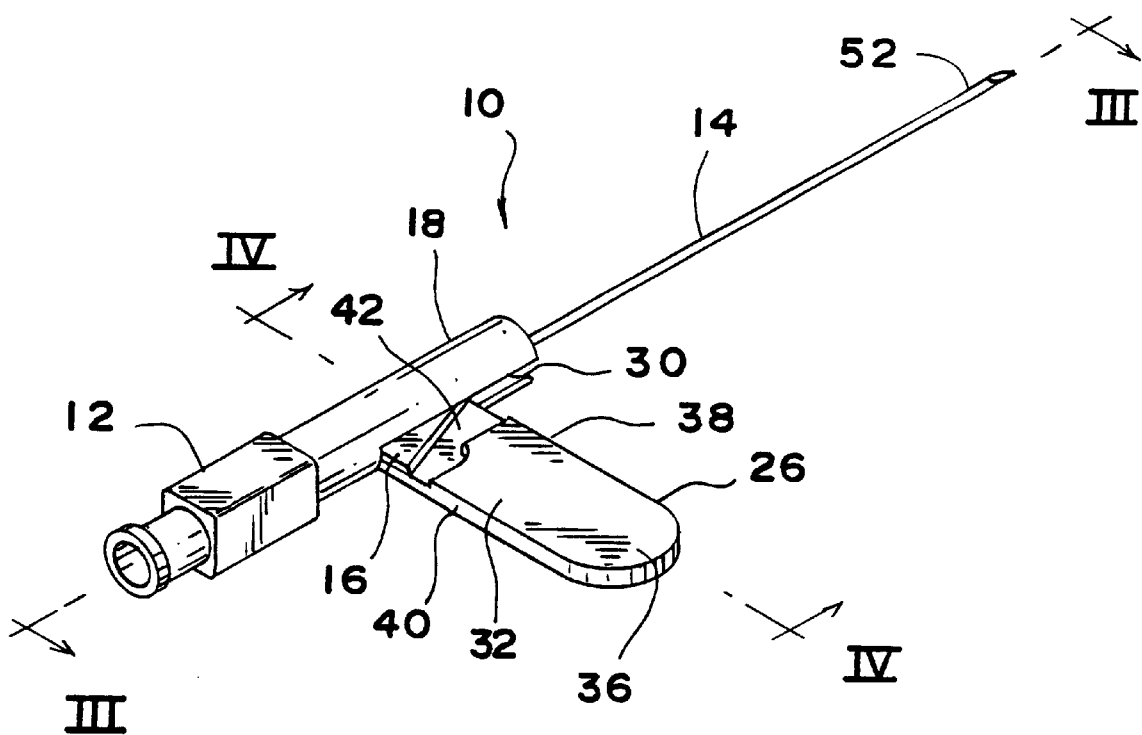
FIG. 1 is a rear perspective view of the present surgical access device.
Figure 2:
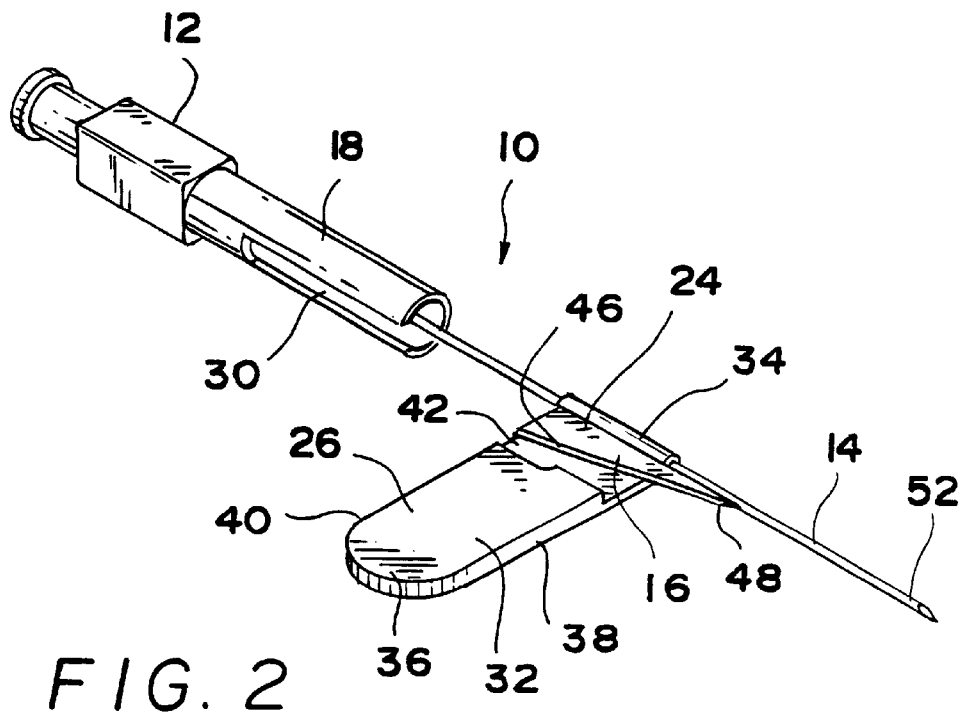
FIG. 2 is a forward perspective view of the present surgical access device.
Figure 3:
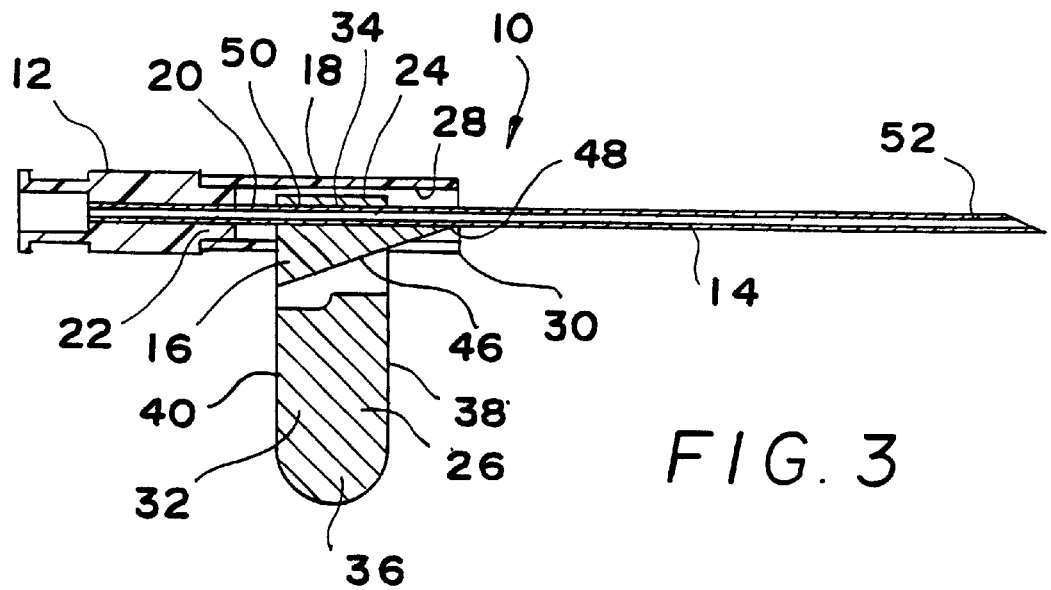
FIG. 3 is a cross sectional view along the line III—III in FIG. 1.
Figure 4:
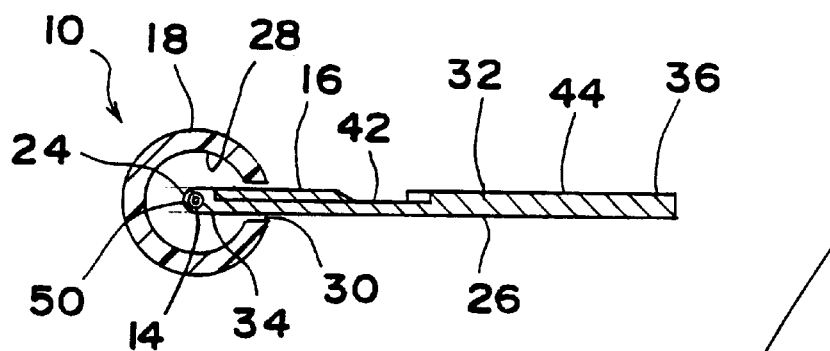
FIG. 4 is a cross sectional view along the line IV—IV in FIG. 1.
Figure 5:
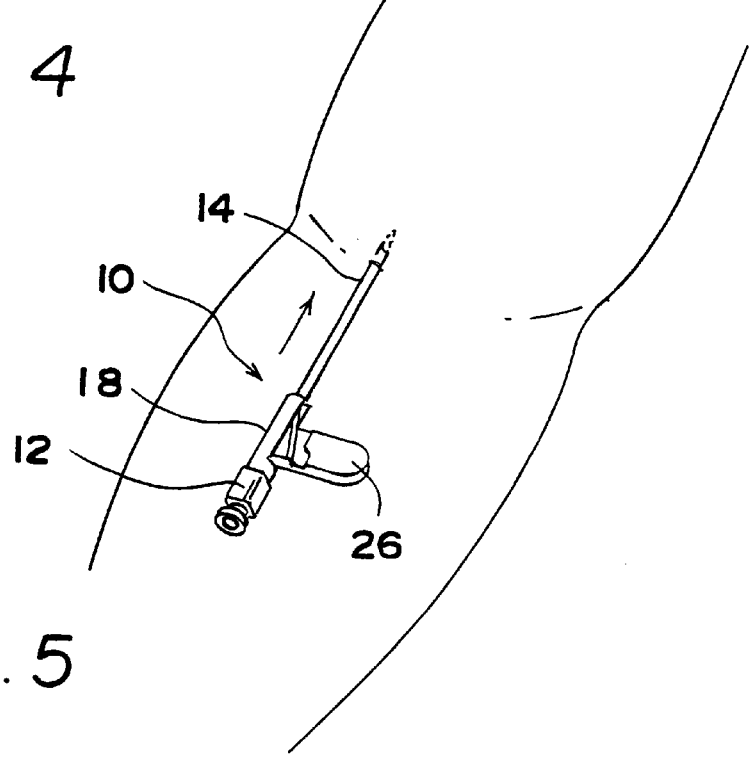
FIGS. 5, 6, 7 and 8 disclose a preferred embodiment of the method associated with use of the present surgical access device.
Figure 6:
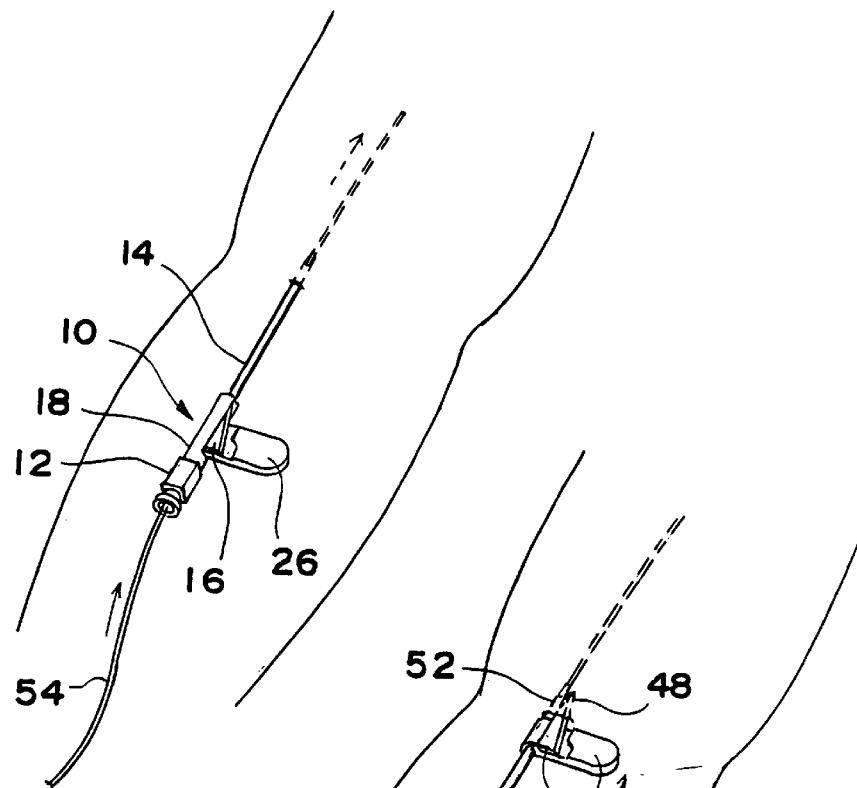
Figure 7:
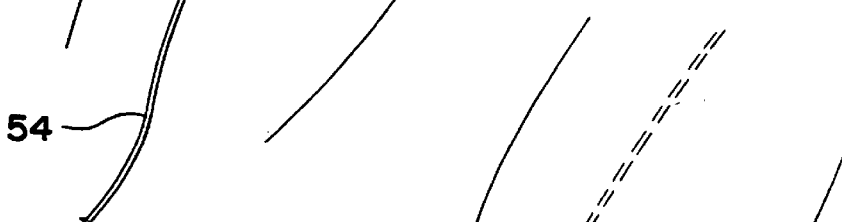
Figure 8:
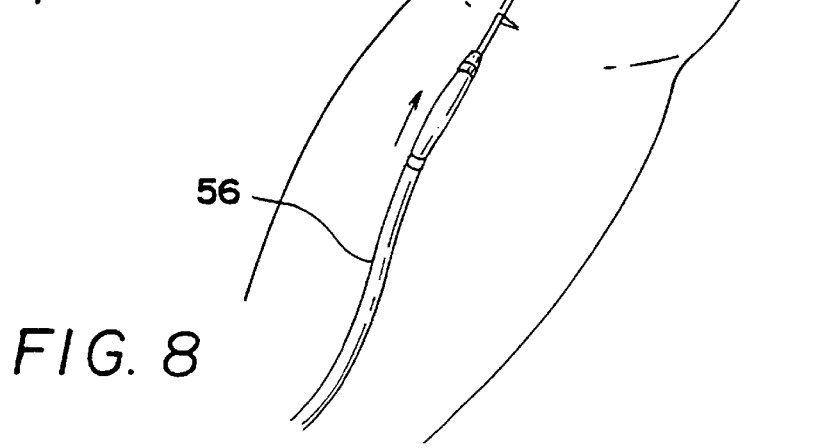

With reference to FIG. 1, a vascular access device 10 is disclosed. The vascular access device 10 generally includes a hub 12 supporting a needle 14 shaped and dimensioned for penetrating tissue in a desired manner. The vascular access device 10 further includes a surgical blade 16 coupled to the needle 14 for sliding therealong to permit controlled incising of tissue surround the needle 14. The vascular access device 10 also includes a surgical blade housing 18 associated with the hub 12 and surrounding a proximal end 20 of the needle 14. The housing 18 is shaped and dimensioned for storing the surgical blade 16 therein during periods of nonuse.

While the present surgical device is primarily intended for use as a vascular access device as described herein, those skilled in the art will appreciate the many other applications for which the present device may find use. With this in mind, the present disclosure should not be construed as limiting the disclosed device to use only in vascular access applications, but rather as a general description for understanding the structure and utility of the present surgical device.

The present vascular access device 10 is adapted for facilitating vascular access, and particularly for facilitating the insertion of a guidewire and associated catheter, without requiring a physician to regularly retrieve instruments from a nearby tray table. The present vascular access device 10 permits needle puncture of an access opening and surgical incision of the adjacent tissue, for example, skin, without requiring the physician to retrieve a traditional surgical blade from a nearby table tray. This functionality is achieved by combining a retractable surgical blade 16 with the access needle 14. In this way, a physician may subcutaneously access the vascular system of a subject with the needle 14, insert a guidewire through the needle 14 via the access opening created by the needle 14, retrieve the surgical blade 16 from its storage position within the housing 18, and incise tissue adjacent to the access opening with the retrieved surgical blade 16 for facilitating the passage of the catheter into the vascular system under the guidance of the previously inserted guidewire.

More specifically, the vascular access device 10 includes a standard needle hub 12 from which a needle 14 extends. As the construction of the hub 12 and needle 14 should be designed to conform with current standards in the practice of medicine, the hub 12 and needle 14 may take a variety of forms without departing from the spirit of the present invention. In general, the needle 14 and hub 12 are shaped and dimensioned for the passage of a guidewire therethrough to facilitate the insertion of a catheter into the vascular system as discussed below in substantial detail.

A blade support housing 18, or container, is secured to the distal end 22 of the hub 12 and extends about the proximal end 20 of the needle 14. The housing 18 is substantially cylindrical and provides a container in which the surgical blade 16 is supported and selectively locked, or fixed, prior to and after use. In accordance with a preferred embodiment of the present invention, the surgical blade 16 is frictionally locked in position within the housing 18 (for example, with a nub (not shown) formed along the body of the surgical blade assembly), although those skilled in the art will certainly appreciate other locking mechanism that may be used without departing from the spirit of the present invention.

Specifically, the housing 18 is sufficiently wide to permit the passage of the first end 24 of the surgical blade assembly 26 between the proximal end 20 of the needle 14 and the inner wall 28 of the housing 18. The housing 18 further includes a longitudinal slot 30 shaped and dimensioned for receiving and storing the first end 24 of the surgical blade assembly 26 when it is withdrawn to its nonuse position adjacent the proximal end 20 of the needle 14.

With reference to FIGS. 1 to 4, the surgical blade assembly 26 is disclosed. The surgical blade assembly 26 is designed to selectively slide along the needle 14 when a physician determines that skin surrounding the inserted needle 14 should be incised. Although a preferred embodiment of the present invention employs a sliding mechanism for coupling the surgical blade assembly and the needle, other coupling mechanism permitting relative movement between the surgical blade and the needle may be used without departing from the spirit of the present invention The surgical blade assembly 26 includes an elongated body member 32 supporting the surgical blade 16. The body member 32 includes a first end 34 and a second end 36, as well as a forward end 38 and a rearward end 40.

The first end 34 of the body member 32 includes a blade recess 42 in which the surgical blade 16 is adhesively bonded. The blade recess 42 is of a depth sufficient to position the blade 16 substantially within the center of the body member 32 with the surface of the blade 16 being recessed below the upper surface 44 of the body member 32. The surgical blade 16 is positioned within the recess 42 such that its forward end, or cutting edge, 46 is aligned with the forward end 38 of the body member 32 and the surgical blade 16 extends forwardly and downwardly to its own pointed tip 48. In this way, and as will be discussed below in greater detail, the pointed tip 48 of the surgical blade 16 will first contact the skin adjacent the needle 14 as the surgical blade 16 is slid along the needle 14 and the cutting edge 46 of the blade 16 will incise the tissue surround the needle 14 as the surgical blade 16 is further advanced downwardly along the needle 14.

Figure 9:
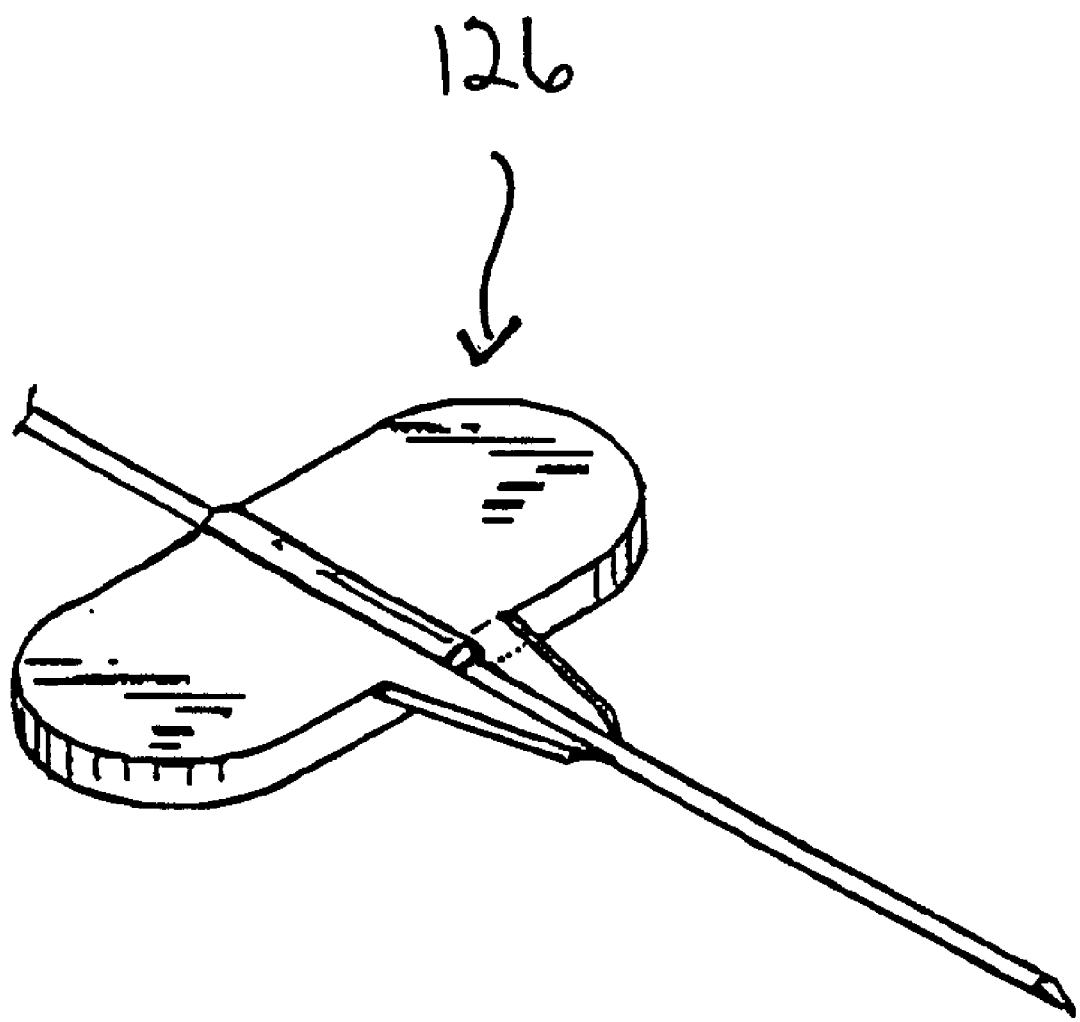
FIG. 9 is a perspective view of an alternate embodiment in accordance with the present invention.

While a specific structure is disclosed for bonding the blade to the body member, those skilled in the art will appreciate the many ways in which the surgical blade assembly may be structured without departing from the spirit of the present invention. In addition, a preferred embodiment is disclosed as including a single blade, although it is contemplated that alternate embodiments may include multiple blades without departing from the spirit of the present invention. For example, and with reference to FIG. 9, a two-sided "arrowhead" shaped surgical blade assembly 126 may be used in accordance with the present invention.

The first end 34 of the body member 32 includes a central through hole 50 shaped and dimensioned for receiving the needle 14 when the vascular access device 10 is fully assembled. The through hole 50 is aligned with the surgical blade 16 and extends along the first end 34 of the body member 32 from the forward end 38 of the body member 32 toward the rearward end 40 of the body member 32. The through hole 50 is positioned so as to maintain the surgical blade 16 in a close relationship with the needle 14, while allowing the surgical blade assembly 26 to slide along the needle 14. With this in mind, the through hole 50 should be formed as close to the surgical blade 16 as possible, without causing interference between the surgical blade 16 and the needle 14 as the surgical blade assembly 26 is slid along the needle 14 in operation.

The second end 36 of the body member 32 acts as a handle which may be gripped by a physician as he or she moves the surgical blade assembly 26 along the needle 14. As such, the second end 36 of the body member 32 may take a variety of grippable forms without departing from the spirit of the present invention.

When fully assembled, and prior to use, the needle 14 is passed through the through hole 50 of the surgical blade assembly 26 and the first end 24 of the surgical blade assembly 26 is positioned within the surgical blade housing 18. Specifically, the slot 30 of surgical blade housing 18 is shaped and dimensioned to receive the first end 24 of the surgical blade assembly 26 with the pointed tip 48 of the surgical blade 16 fully positioned within the confines of the surgical blade housing 18.

In use, and with reference to FIGS. 5, 6, 7 and 8 the vascular access device 10 is retrieved by the physician after the physician determines where to gain access to a patient's vascular system. The needle 14 is then inserted within the vascular system in a conventional manner and a guidewire 54 is inserted therethrough. The guidewire 54 is then manipulated to a desired location.

Once the guidewire 54 is properly positioned within the patient's vascular system, an incision adjacent the needle 14 must be formed to provide an access opening for the passage of a catheter over, or adjacent, the guidewire 54. With this in mind, the physician may now take advantage of the improved functionality offered by the present vascular access device 10. The physician will withdraw the surgical blade 16 from the surgical blade housing 18 by sliding the surgical blade assembly 26 down the length of the needle 14. Movement of the surgical blade assembly is guided in a controlled manner by the fact that the needle 14 is positioned within the through hole 50 formed in the first end 24 of the surgical blade assembly 26 adjacent the surgical blade 16.

As the surgical blade assembly 26 is slid down the needle 14, the pointed tip 48 of the surgical blade 16 will first contact the patient's tissue adjacent to the needle 14. Continued movement of the surgical blade 16 toward the distal end 52 of the needle 14 will cause the surgical blade 16 to incise the tissue adjacent the needle 14 providing a desired access opening for passage of a catheter within the patient's vascular system. Once the tissue surrounding the needle 14 is fully incised, the surgical blade assembly 26 is slid up the needle 14, returned within the surgical blade housing 18 and locked into position. The vascular access device 10 may then be withdrawn from the patient and the procedure completed with the insertion of a catheter.

The vascular access device has been generally described above with reference to the insertion of a guidewire and catheter within the vascular system of a patient. It will be understood by those skilled in the art that the present vascular access device may be used in central venous catheter placement of any kind, including, but not limited to, tunneled and non-tunneled dialysis catheters, Hickman catheters, infusion ports, and any other tunneled and non-tunneled catheters. The present vascular access device may also be used in arterial catheter placement, including, but not limited to, insertion of catheters and sheaths for performing catheterization and cardiovascular interventions. The vascular access device may further be used for a variety of drainage procedures wherein a needle is used to access an abscess cavity/lesion and is exchanged for a catheter to facilitate drainage.

The present vascular access device provides for improved safety as there is no need to take an exposed surgical blade from a tray to the patient and back, thus minimizing the risk of injury to the operators and exposure to blood born pathogens such as HIV and Hepatitis B and C viruses. The vascular access device also provides ease of use for operators. For example, when one performs skin incisions after the insertion of a needle, there is a possibility that the skin incision is not directly adjacent to the needle, thus leaving some tissue between the incision and the needle. This prevents insertion of the catheter and the incision must be revised. With the sliding blade of the present invention, the blade slides over the needle in a highly controlled manner and the possibility of an inaccurate skin incision is eliminated. The present vascular access device also improves efficiency since the skin incision is performed after gaining access to a vessel as opposed to prior techniques requiring that the incision be performed prior to the insertion of the needle into the skin of a patient. This prevents additional skin incisions in the event vascular access is not successful and another access site is required.

While the preferred embodiments have been shown and described, it will be understood that there is no intent to limit the invention by such disclosure, but rather, is intended to cover all modifications and alternate constructions falling within the spirit and scope of the invention as defined in the appended claims.

What is claimed is:

1. A surgical access device, comprising:

a hub supporting a needle shaped and dimensioned for penetrating tissue in a desired manner;

a surgical blade coupled to the needle for movement along the length of the needle such that the surgical blade being selectively moveable along the needle to incise tissue adjacent the needle, wherein the surgical blade forms part of a surgical blade assembly;

the surgical blade assembly includes an elongated body member having a first end and a second end, the surgical blade being secured to the first end of the body member, which forms a through hole shaped and dimensioned for receiving the needle such that the surgical blade assembly being selectively moveable along the needle to move the surgical blade into selective contact with tissue adjacent the needle for incising the tissue, wherein the elongated body member includes a longitudinal axis which is substantially perpendicular to the through hole and, consequently, perpendicular to a longitudinal axis of the needle, and the elongated body member further includes a handle formed along the second end of the body member.

2. The surgical access device according to claim 1, further including a housing positioned adjacent the hub, the housing being shaped and dimensioned for storing the surgical blade when not in use.

3. The surgical access device according to claim 2, wherein the housing includes a slot into which the blade is retracted in its nonuse position.

4. The surgical access device according to claim 2, wherein the housing is substantially cylindrical and surrounds a proximal end of the needle.

5. The surgical access device according to claim 1, wherein the surgical blade slides relative to the needle.

6. A method for surgical access to the vascular system of a patient, comprising the following steps:

percutaneously accessing the vascular system of a subject with a needle of a surgical access device to create an access opening, the surgical access device comprising a hub supporting a needle shaped and dimensioned for penetrating tissue in a desired manner; a surgical blade coupled to the needle for movement along the length of the needle such that the surgical blade being selectively moveable along the needle to incise tissue adjacent the needle, wherein the surgical blade forms part of a surgical blade assembly, the surgical assembly including an elongated member having a longitudinal axis substantially perpendicular to the longitudinal axis of the needle, wherein one end of the elongated member forms a through hole for slidingly receiving the needle; the surgical access device further including a housing positioned adjacent the hub, the housing being shaped and dimensioned for storing the surgical blade when not in use;

retrieving a surgical blade coupled to the needle from a storage position within the housing;

moving the surgical blade relative the needle such that the surgical blade incises tissue adjacent the access opening created by the needle.

7. The method according to claim 6, further including the step of returning the surgical blade to the housing after the incision is made.

8. The method according to claim 7, wherein the housing includes a slot, and the step of moving the surgical blade includes removing the surgical blade from within the slot and the step of returning the surgical blade includes returning the surgical blade within the slot.

9. The method according to claim 6, wherein the step of moving includes sliding the surgical blade along the needle.

10. The method according to claim 6, further including the step of inserting a guidewire though the needle and into the vascular system of the subject where the guidewire is manipulated to a desired location.

11. The method according to claim 10, wherein the incision made by the surgical blade is sufficiently large to permit the passage of a catheter therethrough, and the method includes the additional step of inserting a catheter over the previously insert guidewire and through the incision made by the surgical blade.

12. A surgical access device, comprising:

a hub supporting a needle shaped and dimensioned for penetrating tissue in a desired manner;

a surgical blade assembly including an elongated member having a longitudinal axis substantially perpendicular to the longitudinal axis of the needle and a surgical blade coupled to the needle for movement along the length of the needle such that the surgical blade being selectively moveable along the needle to incise tissue adjacent the needle;

the surgical blade includes a cutting edge having a pointed tip, the pointed tip being aligned with and adjacent to the needle such that the pointed tip contacts tissue to be incised adjacent the needle as the surgical blade is moved into contact with the tissue, wherein one end of the elongated member forms a through hole for slidingly receiving the needle; and a housing positioned adjacent the hub, the housing being shaped and dimensioned for storing the surgical blade when not in use.

13. The surgical access device according to claim 12, wherein the housing includes a slot into which the blade is retracted in its nonuse position.

14. The surgical access device according to claim 12, wherein the housing is substantially cylindrical and surrounds a proximal end of the needle.

15. The surgical access device according to claim 12, wherein the housing includes a slot into which the surgical blade is slid and stored when in its nonuse position.

16. The surgical access device according to claim 12, wherein the surgical blade assembly includes a handle.

* * * * *